United States Patent [19]

Münch

[11] Patent Number: 4,700,706
[45] Date of Patent: Oct. 20, 1987

[54] COLD AND WARM PACK FOR PHYSIOTHERAPY AND THE LIKE

[76] Inventor: Walter Münch, Mirabellenweg 2, 7031 Gäufelden 2, Fed. Rep. of Germany

[21] Appl. No.: 825,336

[22] Filed: Feb. 3, 1986

[51] Int. Cl.⁴ ............................ A61F 7/10; F25D 3/08
[52] U.S. Cl. ....................................... 128/403; 62/530
[58] Field of Search ................... 128/402, 403; 62/530

[56] References Cited

U.S. PATENT DOCUMENTS

| | | | |
|---|---|---|---|
| 3,075,529 | 1/1963 | Young | 128/403 |
| 3,463,161 | 8/1969 | Andrassy | 128/403 X |
| 4,204,543 | 5/1980 | Henderson | 128/403 X |
| 4,457,308 | 7/1984 | Golke et al. | 128/399 |
| 4,462,224 | 7/1984 | Dunshee et al. | 62/530 |
| 4,530,220 | 7/1985 | Nambu et al. | 128/402 X |
| 4,596,250 | 6/1986 | Beisang et al. | 128/403 X |

FOREIGN PATENT DOCUMENTS

| | | |
|---|---|---|
| 0036910 | 10/1981 | European Pat. Off. . |
| 1930103 | 12/1965 | Fed. Rep. of Germany . |
| 8130330 | 3/1983 | Fed. Rep. of Germany . |
| 1600505 | 10/1981 | United Kingdom . |

OTHER PUBLICATIONS

Search Report of German application P 34 11 357.6.

*Primary Examiner*—Anton O. Oechsle
*Attorney, Agent, or Firm*—Steele, Gould & Fried

[57] ABSTRACT

A temperature-storage pack has a tightly bonded sleeve partly filled with temperature-storage material that is kneadable, non-flowing and lacking component builder substances and included air. The sleeve is formed from a vacuum-formed cup-shaped section bonded to a planar part.

23 Claims, 3 Drawing Figures

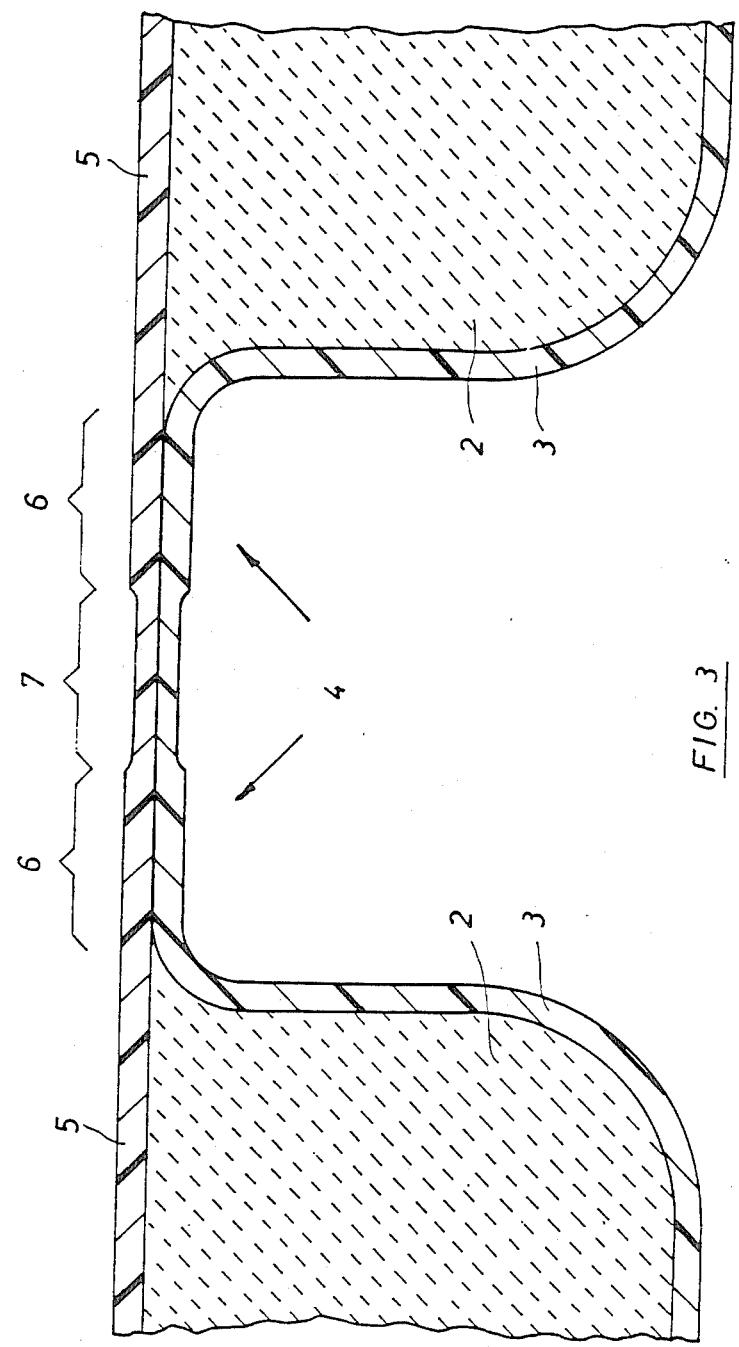

COLD AND WARM PACK FOR PHYSIOTHERAPY AND THE LIKE

BACKGROUND OF THE INVENTION

The present invention relates to a cold and warm pack for physiotherapy and the like with a tightly bonded or welded sleeve made from a flexible foil, film or sheet and a heat-storing or cold-storing filling.

Hot and cold compresses and poultices have long been used as a therapeutic aid in the treatment of bruises, strains and similar injuries and are highly esteemed by Doctors and patients, because they can be applied without difficulty to the parts of the body to be treated, prevent the formation of unnecessary swelling and rapidly act in a soothing manner. The same applies with regard to the packs of the aforementioned type, which have the advantage compared with the above-indicated compresses and poultices that they can be applied dry, which is appreciated by the patient.

Initially such packs filled with water, so that they could be heated or cooled without difficulty in water bath. A more pronounced or longer-lasting cooling action of such packs could be obtained by placing them in a refrigerator or deep-freeze. However, longer storage in a refrigerator or deep-freeze caused the contents to become solidly frozen, with the disadvantage that the originally flexible pack was converted into a rigid structure which, on application to an uneven surface, e.g. a knee joint, assumed non-uniform contact and consequently a non-uniform heat transfer. Therefore packs of the aforementioned type were developed, whose filling consisted of a glycol—water mixture, which did not change as rapidly into a rigid structure. However, such packs have not proved completely satisfactory in practice because it was also not possible to prevent in their case that the liquid content thereof would be non-uniformly distributed when placed on an uneven substrate, so that they fail to ensure a uniform heat transfer.

It has therefore been proposed to place a foam insert impregnated with a heat-storing or cold-storing fluid in the interior of the pack sleeve. However, as a result of the given shape of the foam insert, the ability of such a pack to adapt to an uneven surface is limited. In addition, this foam insert unnecessarily decreases the heat and cold storage capacity of the pack. The latter also applies with respect to those packs, whose interior contains closed-cell foam bodies, e.g. balls, in addition to heat or cold-storing fluid, because such foam bodies also reduce the heat or cold storage capacity of the pack. In addition, the known packs freeze when kept for long periods at below $-15°$ C.

SUMMARY OF THE INVENTION

The problem of the invention is therefore to provide a pack of the aforementioned type, which can be adapted without difficulty to an uneven substrate and which ensures a uniform heat transfer, while having a good heat or cold storage capacity.

According to the invention, this problem is solved by a pack of the aforementioned type containing a kneadable and no longer freely flowing, heat or cold-storing filling, i.e. a filling which, without losing its resiliency, can deform in such a way that it retains its given shape and does not "flow away" following gravity. This filling is preferably kneadable in a temperature range of at least $-30°$ C. to $+50°$ C., so that the inventive pack can be used in a correspondingly dimensioned temperature range.

The filling of the pack according to the invention can contain a thickener, preferably an inorganic thickener. According to a particularly preferred embodiment, the thickener in the filling is insoluble and in particular a solids powder. Thickeners based on silicic acid are suitable. e.g. based on pyrogenic or precipitated silicic acid, as are commercially available under the trade name Aerosil. Other additives bringing about a swelling action are also suitable as thickeners and can give the filling material e.g. gelatinous or thixotropic properties.

The filling of the pack according to the invention preferably contains water, as well as a salt and/or organic antifreeze, the latter preferably being based on glycol, particularly propylene-glycol.

The filling of the pack according to the invention is preferably free from large builder substances or elements and in particular free from those having a particle size over 1 mm, so that the kneading shaping of the pack is ensured. If insoluble fillers are used for thickening purposes, then their content in the filling material is preferably at the most such that the volume proportion of the liquid continuous phase is greater than the pore volume of the insoluble fillers.

The filling is preferably vacuum packed in the envelope or sleeve associated therewith, said sleeve preferably being formed from two tightly bonded together foil or film portions, whereof one has a cup-like construction including an all-round edge or rim, whereas the other is planar. The cup-shaped sleeve portion can be a deep-drawn part. The latter has the advantage that the pack can be produced, filled and closed in a single apparatus using two foil webs.

The pack according to the invention is preferably constructed in such a way that in the unshaped state it is substantially flat and has a substantially rectangular cross-section.

A good deformability is obtained if the pack is less than 50% filled, the degree of filling thereof being dependent on its dimensions, i.e. the larger the pack the smaller can be its degree of filling.

In the unshaped state, the pack thickness is 6 to 20 mm and preferably 8 to 15 mm. The preferably substantially temperature-independent viscosity of the filling can be between 20,000 and 200,000 poises, particularly between 50,000 and 150,000 poises. The preferred viscosity range is between 80,000 and 100,000 poises.

The parts forming the sleeve are preferably in each case made from a composite foil in order to increase the strength.

The pack according to the invention can be connected to at least one, correspondingly constructed pack, preferably via a rim or edge common to both packs and which is preferably a longitudinal edge. Between adjacent packs, there is preferably a strip which is wide enough to enable the two packs to be folded over against one another.

BRIEF DESCRIPTION OF THE DRAWINGS

The invention is described in greater detail hereinafter relative to a non-limitative embodiment and with reference to the attached diagrammatic drawings, wherein:

FIG. 3 is the detail designated III in FIG. 2 on a larger scale.

DETAILED DESCRIPTION OF THE INVENTION

Figures 1, 2:
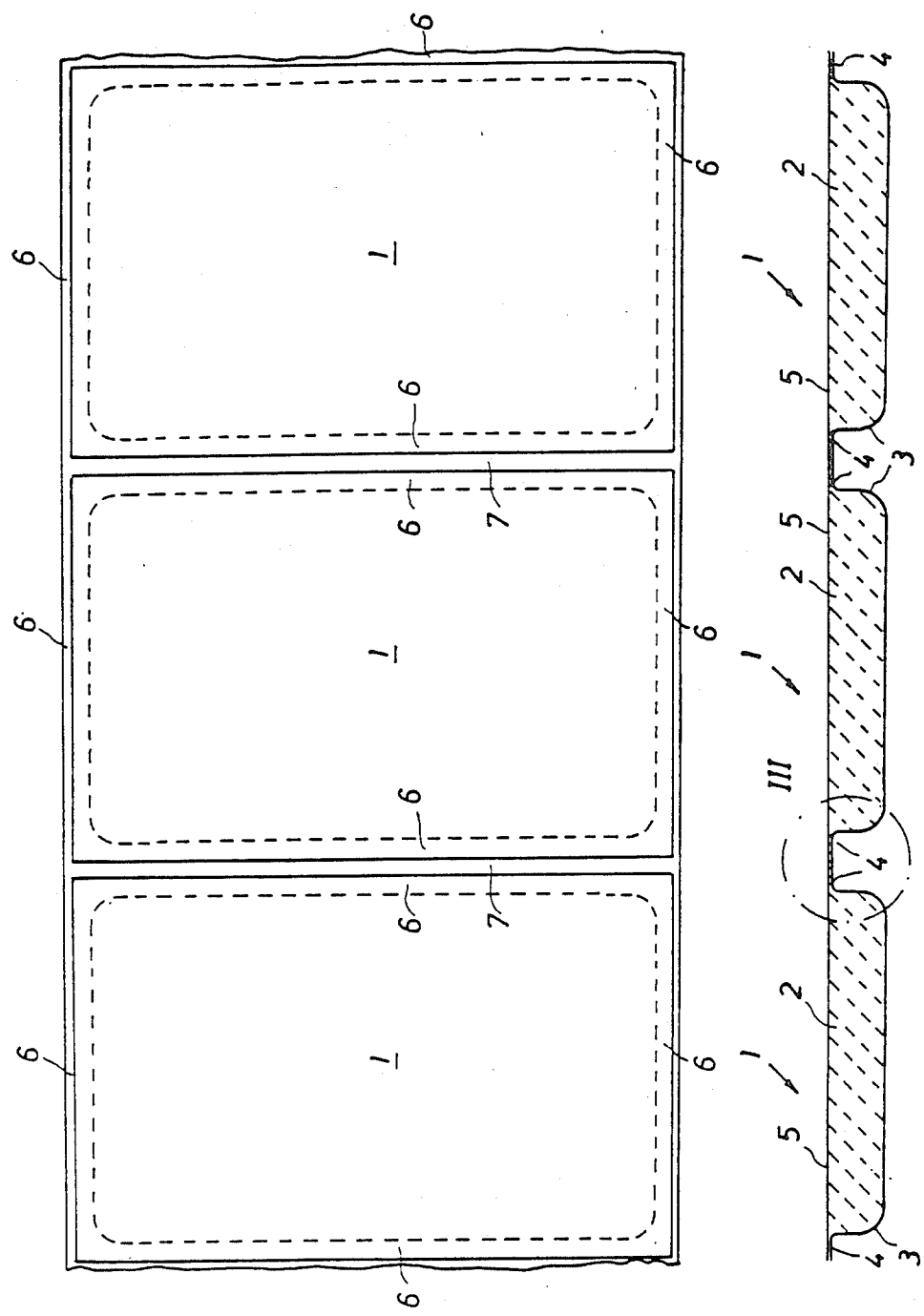
FIG. 1 is a plan view of three interconnected packs according to the invention.
FIG. 2 is a longitudinal section through the packs shown in FIG. 1.

The rectangular packs 1 shown in plan view in FIGS. 1 and 2 in each case comprise a sleeve filled with a filling 2, and three sleeves in each case comprising two tightly bonded together, flexible foil or film portions, between which the filling 2 is vacuum-packed. One of these foil portions is constructed as a cup 3, provided with an all-round flanged edge 4, whereas the other of said foil portions is planar, forming a cover 5. The cup-shaped foil portions 3 are produced from a composite foil in a deep drawing process (i.e., vacuum forming) and are connected by means of a strip 7 joining their edges 4.

The foil portion 3, 5 forming the three packs 1 are bonded to one another and namely in the region 6 surrounding the packs in such a way that the foils there have a structured and preferably slightly burled surface, whilst there is a smooth surface in the intermediate region 7. In the surface-smooth region 7, the three packs can be separated from one another without difficulty by scissors or a sharp knife, so that three individual packs are obtained.

All three packs 1 are uniformly filled with a filling quantity, which corresponds roughly to one third of the filling quantity which can be housed in their sleeves in the case of a corresponding bulging of the three packs 1. As a result, the three packs can be shaped without loss of resiliency, which would not be possible if the sleeves were completely filled. The fillings 2 of the three packs 1 can be shaped, kneaded and displaced in a random manner, i.e. pressed away due to the limited degree of filling between the pack walls and in this way the pack can be adapted to the particular substrate, without any tendency to recover a shape due to by the resiliency of the sleeve or filling.

Filling 2 of packs 1 comprises a substantially non-flowable mixture of water, glycol, salt and finely dispersed silicic acid, the latter having a fineness such that the individual particles are not visible to the eye. The material is in fact turbid, but still translucent. The salt, water and glycol contents can be varied within wide limits and are preferably matched to one another in such a way that the filling material does not freeze at $-30°$ C., i.e. can still be adequately shaped at these temperatures. The mixture of water, common salt, propyleneglycol and Aerosil has the advantage that over substantially the entire temperature range of $-30°$ to $+50°$ C. at which the pack is normally used, it has a substantially constant viscosity. The viscosity can be largely predetermined or set by varying the Aerosil content in the mixture and namely within the range at which the material maintains its given shape, but is still readily kneadable, i.e. can be closely adapted in full-surface manner to the body part to which the pack is to be applied.

The filling material used in the present example comprises the following constituents:
58% $H_2O$
16% NaCl
16% 1,2 Propylene-glycol
9.5% Aerosil
0.5% Propyleneoxide-ethyleneoxide blockpolymer.

In general and as a function of requirements, the filling material composition can be varied within wide limits. Preferred forms contain:

0–70 and particularly 40–64% $H_2O$
0–24 and particularly 10–20% NaCl
5–90 and particularly 10–20% glycol
5–10 and particularly 8–10% dispersed, precipitated or pyrogenic silicic acid
0–1 and particularly 0.5% propyleneoxide-ethyleneoxide blockpolymer.

What is claimed is:

1. A temperature storage pack for physiotherapy and the like, comprising: a tightly bonded sleeve made from a flexible foil, the foil having two tightly-bonded together foil portions, one of the portions being cup-shaped and having a peripheral flanged edge, the other of the portions being planar and having a periphery bonded to the flanged edge of the cup-shaped portion, the cup-shape portion being deep-drawn; and, a temperature-storing filling in the sleeve, the sleeve being only filled to part of its filling capacity and substantially without the inclusion of air, the filling being a kneadable, non-freely flowing filling material having no discrete bodies large enough to be visible to the eye.

2. A pack according to claim 1 wherein the filling material is kneadable in the temperature range of at least $-30°$ C. to 30 50° C.

3. A pack according to either of the claims 1 or claim 2 wherein the filling material contains a thickener.

4. A pack according to claim 3, wherein the thickener is insoluble in the remaining constituents of the filling material.

5. A pack according to claim 3 wherein the thickener is based on silicic acid.

6. A pack according to claim 3, wherein the thickener is inorganic.

7. A pack according to claim 4, wherein the thickener is based on silicic acid.

8. A pack according to claim 1, wherein the filling material contains water, at least one of organic anti-freeze and at least one salt.

9. A pack according to claim 1, wherein the filling material contains an antifreeze based on glycol.

10. A pack according to claim 9, wherein the filling material contains an anti-freeze based on propylene-glycol.

11. A pack according to claim 1, wherein the filling material is free from builder substances in a form of bodies having a particle size over 1 mm.

12. A pack according to claim 1, wherein the sleeve is flat in an unshaped state and has a substantially rectangular cross-section.

13. A pack according to claim 1 wherein the sleeve of the pack is filled to less than 50%.

14. A pack according to claim 13, wherein the sleeve is filled between 15 and less than 50%.

15. A pack according to claim 1, wherein the pack has a thickness of 6 to 20 mm in an unshaped state.

16. A pack according to claim 15, wherein the pack has a thickness of 8 to 15 mm in the unshaped state.

17. A pack according to claim 1 wherein its filling has a viscosity between 20,000 and 200,000 poises.

18. A pack according to claim 17, wherein the filling has a viscosity between 50,000 and 150,000 poises.

19. A pack according to claim 17, wherein the filling has a viscosity between 80,000 and 100,000 poises.

20. A pack according to claim 1 wherein the portions forming the sleeve are in each case constituted by a composite foil.

21. A pack according to claim 1 wherein the pack is joined to at least one further, correspondingly constructed pack, by means of an edge common to both packs, the edge subdividing the two packs being sufficiently wide that the two packs can be flapped against one another.

22. A pack according to claim 21, wherein the pack and the correspondingly constructed pack are joined along a longitudinal edge common to both packs.

23. The pack of claim 1, wherein the filling material is vacuum packed in the sleeve.

* * * * *